United States Patent [19]

Mühlbock et al.

[11] 4,199,544
[45] * Apr. 22, 1980

[54] READ-OFF DEVICE FOR MEDICAL SAMPLES

[75] Inventors: Franz Mühlbock, Münich; Akos Kärpaty, Otterfing; Wilhelm Pross, Münich, all of Fed. Rep. of Germany

[73] Assignee: Compur-Electronic Gesellschaft mit beschrankter Haftung, Munich, Fed. Rep. of Germany

[*] Notice: The portion of the term of this patent subsequent to Dec. 5, 1995, has been disclaimed.

[21] Appl. No.: 902,626

[22] Filed: May 4, 1978

Related U.S. Application Data

[63] Continuation of Ser. No. 750,769, Dec. 15, 1976, Pat. No. 4,128,400.

[51] Int. Cl.$^2$ .............................................. G01N 33/16
[52] U.S. Cl. ................................. 422/72; 422/102; 350/243; 233/1 R
[58] Field of Search .................. 422/101, 102, 72; 233/1 R, 26, 1 A; 350/243

[56] References Cited

U.S. PATENT DOCUMENTS

| 1,367,879 | 2/1921 | Laird | 350/243 |
|---|---|---|---|
| 1,590,613 | 6/1926 | Benedict | 350/243 |
| 2,011,945 | 8/1935 | Mathi | 350/243 |
| 3,512,875 | 5/1970 | Viollet | 350/243 |
| 3,533,628 | 12/1970 | Rosenberg | 350/243 X |
| 3,810,737 | 5/1974 | Geist et al. | |

Primary Examiner—R. E. Serwin
Attorney, Agent, or Firm—Stonebraker, Shepard & Stephens

[57] ABSTRACT

A device for reading the results of centrifugal separation of test samples such as samples of blood. The centrifugal separation apparatus is provided with a housing having a hinged cover having a magnifying lens built into it, either as a lens shaped portion of a plastic cover, or as a separate glass lens attached to the cover. Arms on the hinged cover, engaging with abutment portions on a stationary part of the housing, define a position of the cover which is most appropriate for reading the results.

1 Claim, 6 Drawing Figures

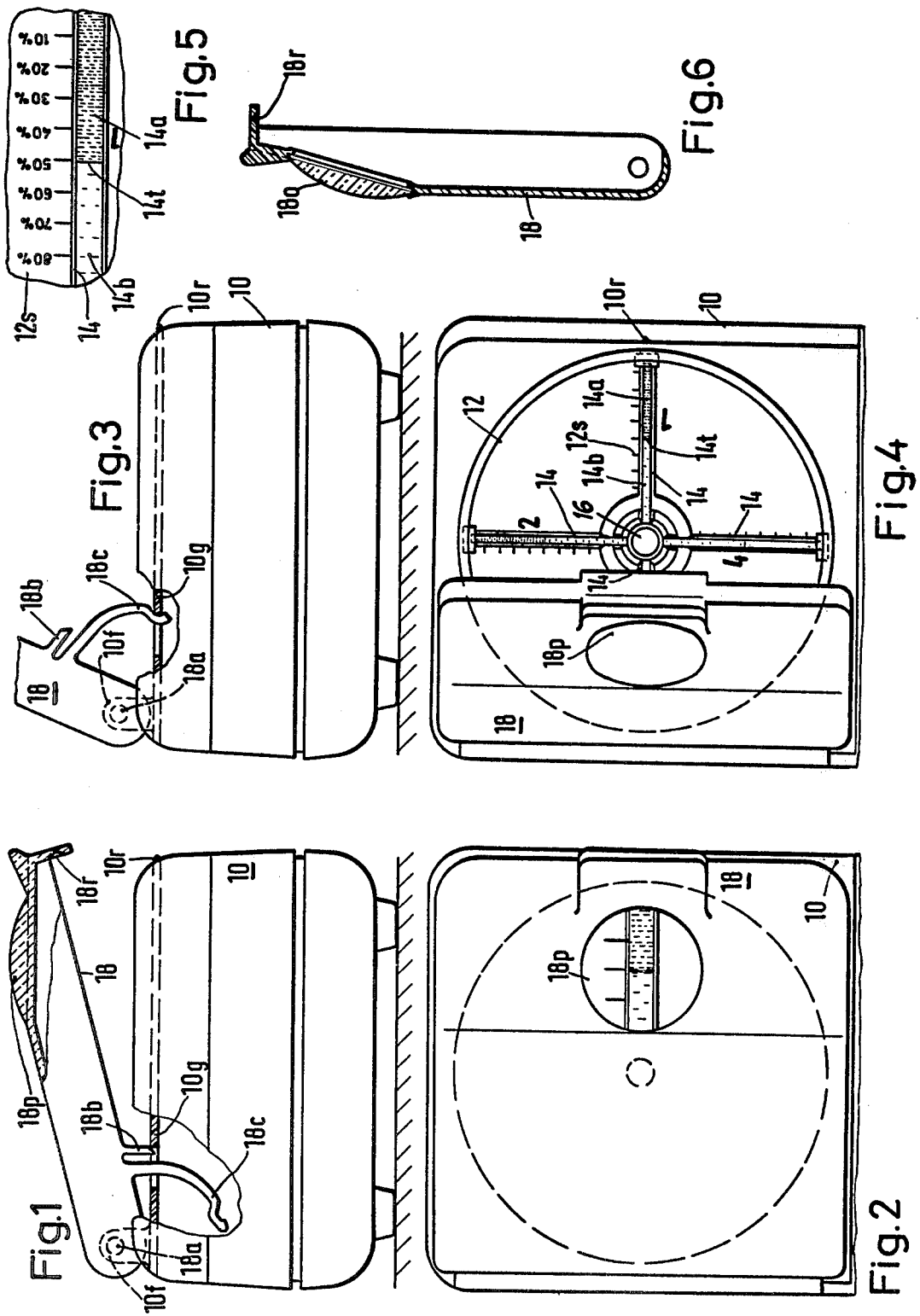

READ-OFF DEVICE FOR MEDICAL SAMPLES

CROSS REFERENCE TO RELATED APPLICATION

This application is a continuation of application Ser. No. 750,769, filed Dec. 15, 1976 now U.S. Pat. No. 4,128,400, granted Dec. 5, 1978.

BACKGROUND OF THE INVENTION

This invention relates to a read-off device for a medical testing appliance in which the sizes of columns of liquid held separated in a vessel of rod form, such as a capillary tube, are to be read-off, particularly in the case of component columns of a test sample separated by a centrifuging operation.

An object of the present invention to provide a simple and inexpensive device for the reading-off of the measuring values without the use of troublesome intermediary or comparison means. This object is met in the present invention by the fact that a read-off scale is arranged along the vessel and in a fixed relation to the latter, and the junction between the columns serves as a marker co-ordinating with the read-off scale. By these means the measuring values to be determined can be read from or beside the capillary tube or other vessel and the determination of the measurements thereby is greatly simplified and accelerated.

In the preferred embodiment of the invention an optical enlarging means is associated with the appliance to enable the read-off scale and the marker to be observed simultaneously. This greatly increases the accuracy of the measuring.

To prepare the measuring liquids for medical test purposes use is frequently made of a centrifuge, in the rotor of which a plurality of capillary tubes filled with test samples are clamped for centrifuging. The rotor holding the tubes is within a housing which can be closed by a pivoted cover. In this type of appliance it is advantageous, in accordance with a further feature of the invention, to make the optical enlarging means in the form of a lens which is arranged in the cover and can be brought with the latter into a predetermined read-off position, a read-off scale being provided in the rotor along each capillary tube. The predetermined read-off position is conveniently determined by a lateral arm of the cover which serves as an abutment cooperating with a counter abutment on the housing of the appliance. The lens can be secured in the cover as a separate element. The cover can however be made of transparent material and formed into a lens at a specific part of the material.

BRIEF DESCRIPTION OF THE DRAWINGS

FIG. 1 is a side elevational view of a device in accordance with a preferred embodiment of the invention with parts broken away and parts in section, illustrating the cover in its read-off position;

FIG. 2 is a plan of the device shown in FIG. 1;

FIG. 3 is a view similar to FIG. 1 but with the cover in a different position;

FIG. 4 is a plan of the parts in the position illustrated in FIG. 3;

FIG. 5 is an enlarged view of a vessel containing a test sample and an associated scale; and FIG. 6 is a sectional view through a modified form of hinged cover.

DESCRIPTION OF THE PREFERRED EMBODIMENT

The centrifuge comprises a multi-part housing 10, installed in which is an electric driving motor for a rotor 12 of plate form. Four like capillary tubes 14 of predetermined content and predetermined lengths can be mounted radially in this rotor and clamped by means of a clamping button 16. The details of a clamping device of this nature may for example take the form described in the copending patent application of Wolfgang König, Ser. No. 732,218, filed Oct. 14, 1976, (now U.S. Pat. No. 4,052,164, granted Oct. 4, 1977) or the copending patent application of Otto Wienchol and Franz Mühlböck, Ser. No. 732,219, filed Oct. 14, 1976, (now U.S. Pat. No. 4,052,165, granted Oct. 4, 1977) and therefore need not be further elaborated here.

Before the commencement of the centrifuging operation the rotor 12 with the capillary tubes 14 clamped therein is closed by a cover 18 pivotally mounted by pins 18a in two apertured lugs 10f of the housing 10. The cover 18 has a catch 18r which in the closed position of the cover engages resiliently with a catch projection 10r of the housing 10.

The cover is preferably made of transparent plastic material and a predetermined portion thereof is shaped to provide a magnifying lens 18p. The cover 18 is provided at one side wall with two downwardly extending projections 18b and 18c which are resilient in a direction radially with respect to the hinge pins 18a. Projection 18b cooperates with an abutment 10g of the stationary housing 10 and defines the read-off position of the cover 18 (FIGS. 1 and 2). The other projection 18c serves as a resilient end catch for retaining the cover 18 in its open position (FIGS. 3 and 4) when the capillary tubes are being inserted and clamped or being removed. Laterally alongside each capillary tube 14 in the rotor 12 is a scale 12s, for example impressed into the material of the rotor and made of a color which is readily visible. Measurement numbers in percentages are associated with the scale markings.

The transparent capillary tubes 14 used for a specific medical test are for example filled with the blood of the patients to be tested, clamped in the centrifuge, and subjected to a centrifuging operation. This produces in each capillary tube two columns of part components, namely an outwardly disposed column 14a with blood clots and an inner column 14b with blood plasma. The two columns are separated by a junction line 14t (FIG. 5) which is clearly visible. Since each capillary tube 14 is full, its total volume can be expressed as 100% for each complete length, further values being provided along the capillary tube 14 in the rotor 12 in like partial spacings within this area. Thus as soon as the cover 18 is brought into the read-off position according to FIGS. 1 and 2, the proportion of the two columns to the total volume of the capillary tube can be directly read-off. In the case of the capillary tube 14 which is in position "1" (FIG. 4) and which is shown enlarged in FIG. 5, the measurement for the column 14a reads 51% and for column 14b correspondingly the value 49% of the total volume, thus making 100%.

The rotor 12 is turned by hand until all the capillary tubes are successively brought into the read-off position under the lens 18p, so that their values can be read-off and noted down.

Instead of the magnifying lens 18p being formed directly in the transparent plastic material of which the cover is made, a separate magnifying lens 180 of optical glass can be inserted in the cover 18 as illustrated in FIG. 6, if a particularly powerful optical enlargement is required.

It is also to be mentioned that the method of reading-off the percentage values in accordance with this invention can also be used for other medical test apparatus in which the values of the component part columns are to be measured in a vessel and automatically read-off.

What is claimed is:

1. A centrifuge device for centrifuging medical samples to separate the samples into visually distinct components and for measuring the proportions of such components without removing the centrifugal samples from the centrifuge, said centrifuge device comprising
   (a) a centrifuge rotor rotatable about an axis,
   (b) means for clamping on said rotor a plurality of tubular containers each open at both ends and each adapted to be completely filled with a sample to be tested, and each arranged radially with respect to said axis,
   (c) each of said containers being of the same length and each being clamped, during rotation of said rotor, in a definite predetermined location on said rotor,
   (d) a reading scale marked on said rotor alongside the clamped location of each of said containers,
   (e) each reading scale being graduated in percentage graduations from 0 to 100,
   (f) the zero graduation of each scale being precisely at one end of its associated container and the 100 graduation of the scale being precisely at the opposite end of its associated container when the container is in clamped position on the rotor, and
   (g) a housing surrounding said rotor and said containers thereon.

* * * * *

UNITED STATES PATENT AND TRADEMARK OFFICE
CERTIFICATE OF CORRECTION

PATENT NO. : 4,199,544
DATED : April 22, 1980
INVENTOR(S) : Franz Mühlböck, Akos Kárpaty, and Wilhelm Pross It is certified that error appears in the above–identified patent and that said Letters Patent are hereby corrected as shown below:

In the heading of the patent, add the following:

-- [30] Foreign Application Priority Data

December 17, 1975 Germany........... 2556915 --

Signed and Sealed this

Fifteenth Day of July 1980

[SEAL]

Attest:

SIDNEY A. DIAMOND

Attesting Officer  Commissioner of Patents and Trademarks